(12) United States Patent
Le Berre et al.

(10) Patent No.: US 9,469,840 B2
(45) Date of Patent: Oct. 18, 2016

(54) DEVICE FOR GUIDING CELL MIGRATION AND METHOD OF GUIDING CELL MIGRATION IMPLEMENTING SUCH A DEVICE

(71) Applicants: INSTITUT CURIE, Paris (FR); CENTRE NATIONAL DE LA RECHERCHE SCIENTIFIQUE—CNRS, Paris (FR); SOCIETE DE DEVELOPPEMENT ET DE RECHERCHE INDUSTRIELLE, Chenove (FR)

(72) Inventors: Maël Le Berre, Paris (FR); Matthieu Piel, Paris (FR); Yanjun Liu, Courbevoie (FR)

(73) Assignees: INSTITUT CURIE, Paris (FR); SOCIETE DE DEVELOPPEMENT ET DE RECHERCHE INDUSTRIELLE, Chenove (FR); CENTRE NATIONAL DE LA RECHERCHE SCIENTIFIQUE—CNRS, Paris (FR)

( * ) Notice: Subject to any disclaimer, the term of this patent is extended or adjusted under 35 U.S.C. 154(b) by 171 days.

(21) Appl. No.: 14/345,836

(22) PCT Filed: Sep. 17, 2012

(86) PCT No.: PCT/FR2012/052077
§ 371 (c)(1),
(2) Date: Mar. 19, 2014

(87) PCT Pub. No.: WO2013/041803
PCT Pub. Date: Mar. 28, 2013

(65) Prior Publication Data
US 2015/0184122 A1    Jul. 2, 2015

(30) Foreign Application Priority Data
Sep. 19, 2011    (FR) ...................................... 11 58317

(51) Int. Cl.
*C12N 5/00* (2006.01)

(52) U.S. Cl.
CPC ......... *C12N 5/0068* (2013.01); *C12N 2533/30* (2013.01); *C12N 2533/32* (2013.01); *C12N 2533/52* (2013.01); *C12N 2535/00* (2013.01); *C12N 2539/00* (2013.01)

(58) Field of Classification Search
CPC ............ C12N 5/0068; C12N 2539/00; C12N 2533/30; C12N 2533/52; C12N 2533/32; C12N 2535/00
See application file for complete search history.

(56) References Cited

U.S. PATENT DOCUMENTS

2009/0248145 A1    10/2009    Chan et al.

OTHER PUBLICATIONS

International Search Report for related International Application No. PCT/FR2012/052077; report dated Nov. 29, 2012.
Goher Mahmud, et al.; *Directing Cell Motions on Micropatterned Ratchets*; journal; Aug. 2009; pp. 606-612; Nature Physics, vol. 5; Macmillan Publishers Limited.

*Primary Examiner* — Taeyoon Kim
(74) *Attorney, Agent, or Firm* — Miller, Matthias & Hull LLP

(57) ABSTRACT

A guiding device in which cells are confined between a support surface and a textured surface of a substrate, said textured surface having an anisotropic three-dimensional structure having a repeating pattern that repeats according to a repeat axis, said repeating pattern having a succession of guide spaces adjacent to one another according to the repeat axis, each of said guide spaces being capable of receiving at least one portion of one of the cells and being oriented according to a direction of anisotropy to guide a movement of the cells in the direction of anisotropy.

33 Claims, 4 Drawing Sheets

DEVICE FOR GUIDING CELL MIGRATION AND METHOD OF GUIDING CELL MIGRATION IMPLEMENTING SUCH A DEVICE

CROSS-REFERENCE TO RELATED APPLICATIONS

This application is a 35 USC §371 U.S. national stage filing of International Patent Application No. PCT/FR2012/052077 filed on Sep. 17, 2012, and claims priority under the Paris Convention to French Patent Application No. FR 11 58317 filed on Sep. 19, 2011.

FIELD OF THE DISCLOSURE

The invention relates to a device for guiding cell migration and to a method of guiding cell migration that makes use of such a device.

In particular, the invention relates to a device for guiding cell migration that comprises a support surface provided with cells, and a substrate, said substrate having a textured surface placed facing the support surface and in contact with the cells placed on the support surface.

BACKGROUND OF THE DISCLOSURE

Cell migration is essential to many physiological processes such as organogenesis or wound healing. In their natural environment, the direction and speed of cell migration is guided by many signals which may be chemical (chemokines) or physical (microenvironment).

In vitro, these phenomena may be reproduced or redirected to impose a direction of migration on cells, for example using chemoattractants, electrical fields, or by modulating the mechanical environment of the cell.

EP-A-1199354 discloses, for example, the formation of a pattern of cells on a surface by chemically controlling the cell migration. In EP-A-1199354, the surface is treated to provide a pre-made pattern consisting of compounds that promote cell growth and other compounds that do not promote cell growth. Cell culturing is then initiated on this pre-made pattern. However, the effectiveness of the control of cell migration by such a system depends mainly on the choice of chemical compounds promoting or preventing cell growth according to the nature of the cultured cells.

US 2007/0009572 describes a method for preparing a micro- or nanotextured biodegradable film comprising channels whose width can vary from 10 μm to 160 μm, on which muscle cells are deposited. Tests show that the muscle cells are aligned relative to each other along the channels, and their morphology changes to assume an elongated form. The aim of this method is not to migrate cells in a preferred direction but to encourage their alignment with each other to obtain a regular cell stack.

US 2009/02481445 also describes a method for guiding the orientation of cells in a three-dimensional structure, using a surface comprising a micro-channel or a series of micro-channels that are parallel to each other, of greater width than the cells to allow the cells to enter them and having an arbitrary cross-section. As in the previous document, the purpose of this method is not to migrate cells in a preferred direction, but to facilitate their alignment with each other.

Mahmud et al. (Nature Physics 2009, 4, pp. 606) propose adhesive ratchet-shaped patterns to guide cell migration. The effect observed is based on a difference in adhesion between the adhesive portions of the channels and the non-adhesive portions of a substrate such that, when the quality of the difference between the adhesive and non-adhesive areas deteriorates over time, guidance of the cell migration is no longer observed. In addition, the linear or ratchet-shaped adhesion in the channels only holds the cells on these adhesive patterns, meaning in a single dimension in a three-dimensional space, and does not allow, for example, tissue organization on a two-dimensional surface. Finally, the patterns described in Mahmud et al. are always perpendicular to the plane formed by the surface carrying the cells.

These methods for redirecting the natural phenomena of cell migration can also have applications in vivo.

US 2009/0093879 proposes an implant having micro- or nanometric three-dimensional patterns on the surface. These patterns allow controlling the adhesion of micro-organisms or fibroblasts to the surface of the implant when it is placed in a living being, thus improving wound healing. US 2009/0093879 suggests that the surface micro- or nanostructures can guide the cells that begin the healing process, allowing them to organize in an ordered manner on the surface of the implant.

However, the control of cell migration in a given direction could also have medical applications which do not involve the forced organization of cells around an implant, such as the directed migration of cells to the surface of a wound or the creation of artificial organs in tissue engineering.

There is therefore a need for new devices for guiding cell migration in a chosen direction, whose effectiveness does not depend on the type of moving cell considered, and which are simple to implement, are minimally invasive for tissues, and remain robust over time.

Guiding cell migration is understood to mean, in the sense of the present application, that the cells are encouraged to migrate in one direction rather than in any other. In other words, guiding the migration breaks the migration symmetry in the direction considered. "Guiding" the cell migration differs from "orienting" the cell migration, the latter being where the cells preferentially migrate in two opposite directions without one of these directions being favored over the other.

SUMMARY OF THE DISCLOSURE

For this purpose, the invention proposes a device for guiding cell migration comprising a support surface provided with cells, and a substrate, said substrate having a textured surface placed facing the support surface and in contact with the cells placed on the support surface such that the cells are confined between the support surface and the textured surface, said textured surface having an anisotropic three-dimensional structure presenting a repeating pattern along a repeat axis, said repeating pattern having a succession of guide spaces adjacent to one another along the repeat axis, each of said guide spaces being capable of receiving at least a portion of one of the cells and being oriented in a direction of anisotropy in order to guide movement of the cells in the direction of anisotropy.

The guiding device according to the invention can thus provide control of cell migration by means of a specific structure in which the confined cells are received and where they move in a preferred direction, regardless of the type of cell used. The guiding device is minimally invasive as it relies on the application of a textured surface to a support surface. Lastly, the guiding device can be obtained in a simple manner, simply by texturing the surface which can be implemented during mass production by molding.

Furthermore, unlike the prior art documents describing channels or microchannels that force the cells into alignment, the present invention guides the cells in a direction of anisotropy, thus forming a network in the plane that is compatible with tissue organization according to a given surface.

The guiding device according to the invention has applications in the fields of dermatology, implants, or tissue engineering.

The terms "anisotropic structure" or "structure having anisotropic geometry" are understood to mean, for the purposes of this application, a structure whose geometry has a defined direction of anisotropy along a given axis. In the context of the invention, the direction of anisotropy of the anisotropic structure is, in particular, the preferred direction of cell migration.

The textured surface may comprise a base surface and the anisotropic three-dimensional structure may comprise a plurality of pairs of guide surfaces, said pairs of guide surfaces being adjacent to each other along the repeat axis and defining the repeating pattern, each pair comprising first and second guide surfaces which extend from the base surface facing one another and which between them define one of the guide spaces.

In particular, the anisotropic three-dimensional structure may comprise a plurality of guide elements projecting from the base surface, said guide elements being adjacent to each other along the repeat axis and each carrying one of the first guide surfaces and one of the second guide surfaces, the first guide surface of one of the guide elements facing the second guide surface of the adjacent guide element.

In one embodiment, the first and second guide surfaces of each pair are adapted so that the direction of anisotropy extends along the repeat axis. In each of pair of guide surfaces, the first guide surface can then be adapted to block movement of the cells in a direction opposite to the second guide surface and the second guide surface can be adapted to allow movement of the cells in a direction opposite to the first guide surface, such that the orientation of the direction of anisotropy is from the first surface towards the second surface. To achieve this, the first guide surface may be perpendicular to the repeat axis and the second guide surface may extend away from the first guide surface along the repeat axis.

In particular, in a first variant, the second guide surface may be perpendicular to the base surface and may have a concavity directed towards the first guide surface. For example, the anisotropic three-dimensional structure may comprise a plurality of rows of triangular projections adjacent along the repeat axis, each of said rows comprising at least two projections aligned along a transverse axis perpendicular to the repeat axis, each of the guide spaces comprising a substantially triangular cavity with a base formed on the first guide surface of one of the rows of triangular projections and a vertex formed on the second guide surface of the adjacent row of triangular projections.

In a second variant, the first guide surface may be perpendicular to the repeat axis and the second guide surface may be sloped relative to a plane perpendicular to the base surface.

In another embodiment, the first and second guide surfaces of each pair are adapted so that the direction of anisotropy extends along a transverse axis perpendicular to the repeat axis. In each of the pairs of guide surfaces, the first and second guide surfaces may then be adapted to block cell movement in one direction of the repeat axis or the other. In particular, the anisotropic three-dimensional structure may comprise a plurality of elongated projections adjacent along the repeat axis, each of said elongated projections extending along the transverse axis, each guide space comprising a groove between the first guide surface of one of the elongated projections and the second guide surface of the adjacent elongated projection.

Furthermore, the guide space may have a maximum dimension, measured between the first and second guide surfaces, that is less than 200 µm, preferably less than 100 µm, and in particular substantially corresponding to a size of the cells, for example between 5 µm and 60 µm, preferably between 15 µm and 30 µm. The guide space may also have a depth of less than 200 µm, preferably less than 100 µm, and in particular less than a size of the cells, for example less than 6 µm.

The substrate may be non-adhesive. In this case, it may consist of a non-adhesive material such as a fluoropolymer or a material rendered non-adhesive by chemical treatment such as grafting of polyethylene glycol (PEG) molecules. The textured non-adhesive surface, meaning the surface to which the cells cannot adhere, can thus be removed without risk of damaging the cells.

As a variant, the substrate may be adhesive.

In addition, the support surface on which the cells move can be an artificial surface such as a cell culture surface (for example a gel), a glass slide, the interior of a microfluidic channel, or a surface of the natural environment of said cells such as the surface of living tissue or the surface of a wound.

The support surface and the textured surface may be spaced apart by a distance of between 0 µm and 10 µm, preferably between 3 µm and 6 µm.

At least one of the surfaces chosen from among the support surface and the textured surface may comprise at least one additional projection for controlling the distance between the support surface and the textured surface. In particular, the additional projection may be in the form of a pillar with a diameter between 100 µm and 500 µm and a height of less than 10 µm, preferably between 3 µm and 6 µm.

Depending on the specific application, the guiding device may be provided in the form of a dressing, an implant, a prosthesis, a support for artificial tissue, a microfluidic channel, a lab-on-a-chip with integrated channels, and said guiding device is preferably a dressing.

In another aspect, the invention proposes a method of guiding cell migration which makes use of a guiding device as defined above, said guiding method bringing the cells placed on the support surface in contact with the textured surface of the substrate so that the cells are confined between the support surface and the textured surface, the cells moving in the direction of anisotropy.

BRIEF DESCRIPTION OF THE DRAWINGS

Other features and advantages of the invention will become apparent from the following description of specific embodiments of the invention given by way of non-limiting example, the description being made with reference to the accompanying drawings in which.

DETAILED DESCRIPTION OF THE DISCLOSURE

Figure 1:
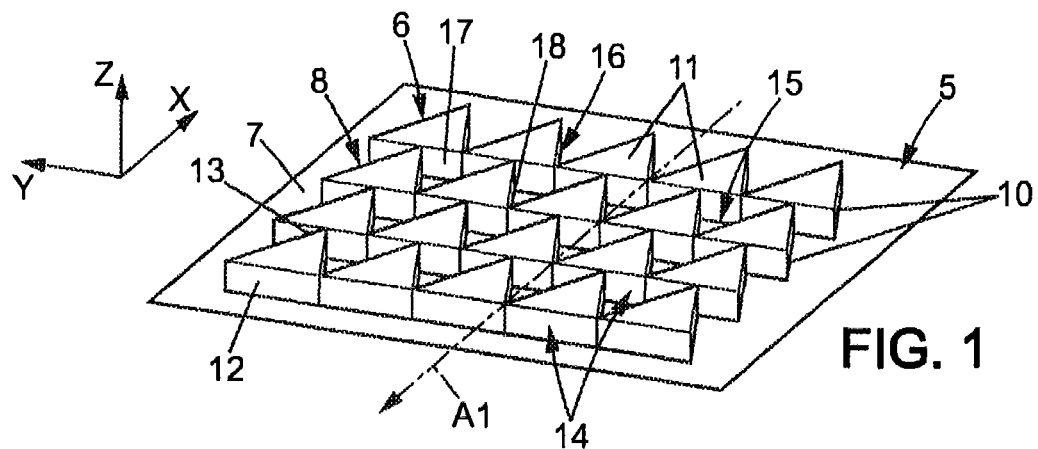
FIG. 1 is a perspective representation of a first embodiment of a substrate of a cell migration guiding device, the substrate having a textured surface with a plurality of rows of triangular projections defining a succession of triangular guide cavities that are adjacent along a repeat axis, the guide cavities being adapted to guide the movement of cells carried on a support surface in one direction of the repeat axis.

In the figures, the same references are used to denote identical or similar elements.

The figures show a cell migration guiding device 1 comprising a support surface 2 provided with cells 3 and a substrate 5 suitable for guiding the movement of cells along an axis and in one of the two directions of the preferred axis.

According to a preferred embodiment, the substrate 5 is not adhesive, meaning that the cells cannot adhere to the substrate 5, to allow removing the substrate 5 from the support surface 2 without damaging the cells, as will be apparent from the following description. Such a non-adhesive substrate 5 is also called an anti-fouling substrate.

The non-adhesive nature of the substrate 5 corresponds to the substrate 5 having low protein adsorption ability and low cell adhesion ability, which in general limits inflammatory reactions.

The non-adhesive materials suitable for the non-adhesive substrate 5 may be superhydrophobic—as is the case for fluoropolymers (for example polytetrafluoroethylene (PTFE))—or gels such as polyacrylamide (PAM) or polyethylene glycol diacrylate (PEGDA).

Alternatively, the non-adhesive substrate 5 may be composed of a material rendered non-adhesive by chemical treatment.

Chemical treatments to render the substrate 5 non-adhesive may, for example, involve grafting on the substrate a monomolecular layer of gel, for example polyethylene glycol (PEG), for example a PEG silanized on the oxides or thiolated on the metals or conjugated with a polyelectrolyte to impart lasting adsorption ability via electrostatic interaction on the substrate 5, as is the case for grafted polylysine-PEG (PLL-PEG).

Preferably, the non-adhesive material is a fluoropolymer or a material rendered non-adhesive by a chemical treatment such as the grafting of molecules, for example polyethylene glycol (PEG) molecules.

However, the substrate 5 may be adhesive, depending on the particular application in which the guiding device 1 is used.

Adhesive materials which are suitable for the adhesive substrate 5 may be hydrophilic or hydrophobic, possibly treated with a cell adhesion promoter, and chosen from among:

biocompatible plastics: for example, polystyrene (PS), commonly used in cell culturing, silicone polymers such as polydimethylsiloxane (PDMS) used in labs-on-a-chip, gels of block copolymer such as styrene-ethylene/butylene-styrene (SEBS), used in the manufacture of dressings, or lactic and glycolic poly acids (PLGA, PLA: hydrophilic) that are biodegradable and can be used for implants or as support for artificial tissue; some of these plastics may advantageously be oxygen plasma-activated to increase their hydrophilicity and promote cell adhesion, ceramics, generally hydrophilic, such as metal oxides or nitrides, for example glass ($SiO_2$), silicon nitride ($Si_3N_4$), titanium dioxide ($TiO_2$) or other; these materials are used in cell culturing, in labs-on-a-chip or in implants; these materials can advantageously be activated by oxygen plasma to increase their hygrophilicity and promote cell adhesion, inert metals such as gold, platinum, palladium, or metals whose oxidized or nitrided surface is stable such as chromium or titanium which are used for implants; advantageously, the metals can be treated with molecules of the thiol family to increase or decrease their capacity for cell adhesion.

It is also possible to promote cell adhesion by chemically treating a support material. One can use:

charged polymers (polyelectrolytes) which strongly adsorb via electrostatic interaction to the oxidized surfaces (naturally, for example the oxides, or artificially by oxygen plasma-activation of the surfaces): examples include poly-L-lysine (PLL) or polyornithine (PORN), or cell adhesion proteins (integrins) or extracellular matrix proteins (fibronectin, laminin, collagen) or peptides mimicking these proteins, such as the RGD pattern. (arginine-glycine-aspartic acid).

Within the scope of the present invention, it is also possible to adjust cell adhesion to the substrate 5 to optimize cell motility. The level of cell adhesion to a substrate 5 can be adjusted by treating the substrate with a ratiometric mixture of adhesive molecules and non-adhesive molecules. For example, a mixture of pLL-PEG and pLL-PEG-RGD, or a mixture of pLL-PEG and fibronectin can be used.

Figure 2:
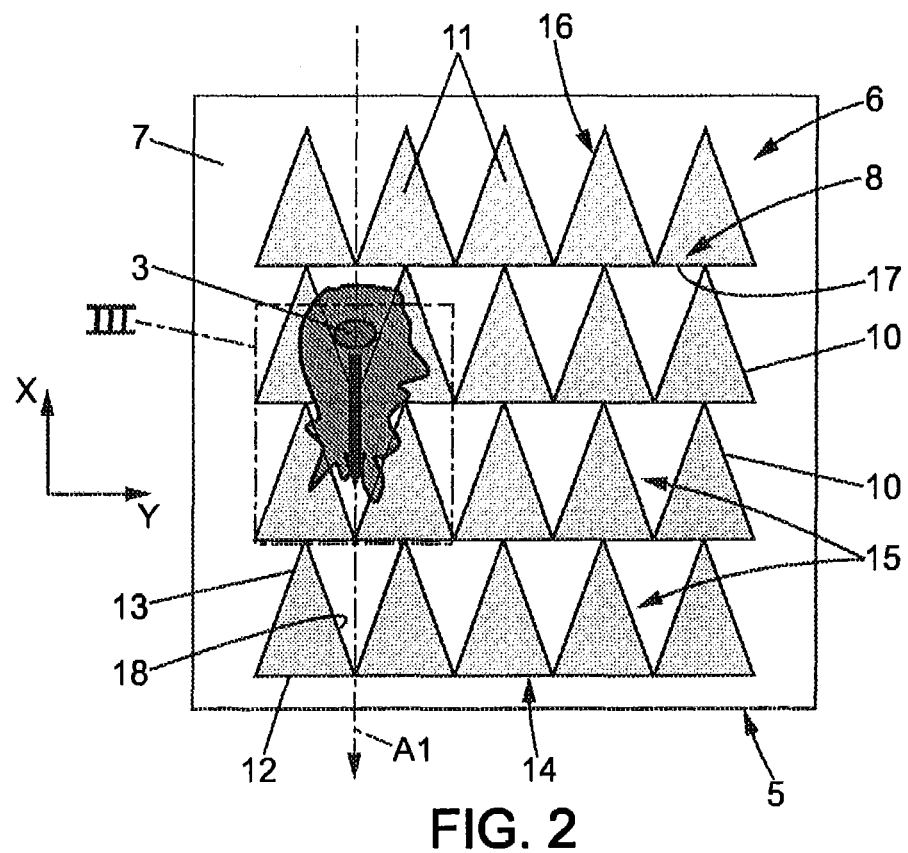
FIG. 2 is a top view representation of the substrate of FIG. 1, where the textured surface is arranged facing a support surface in a guiding device, FIG. 2 showing the movement of a cell between a support surface and the textured surface of the substrate.
Figure 3:
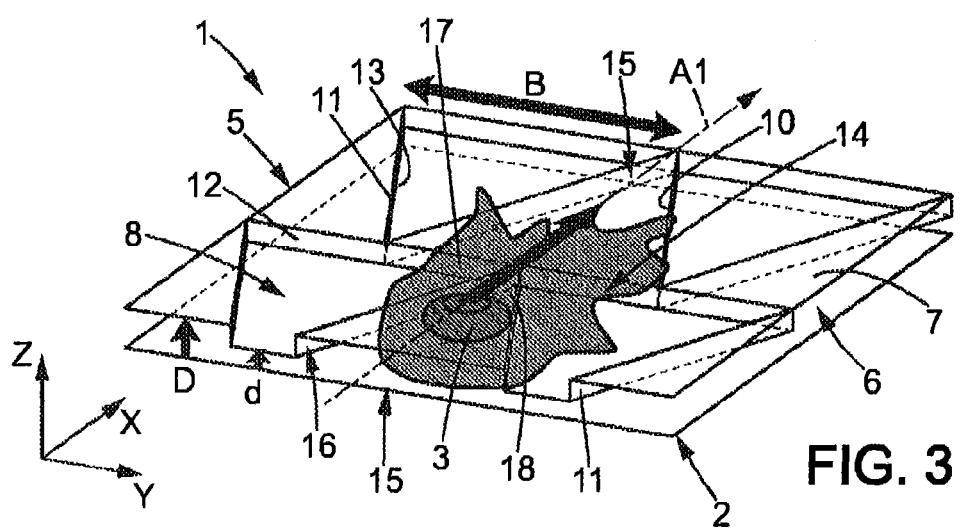
FIG. 3 is a perspective view of the detail denoted III in FIG. 2, along the direction of the cell movement.

The substrate 5 presents a textured surface 6 having a base surface 7 and a three-dimensional anisotropic structure 8 visible in FIG. 1 and shown in phantom lines in the base surface 7 in FIGS. 2 and 3. The anisotropic three-dimensional structure 8 comprises a plurality of guide elements projecting from the base surface 7 along a vertical axis Z perpendicular to the base surface 7. The guide elements are arranged on the base surface 7 so as to be adjacent to one another along a repeat axis X, perpendicular to the vertical axis Z. In the figures, the substrate 5 is represented as flat with a corresponding description of the axes to clarify the orientation and the relative positioning of the elements of the substrate 5. As is apparent from the above and as will be apparent from the following description, particularly of the applications of the guiding device 1, the substrate 5 may be deformable and may have any configuration other than the flat configuration represented.

In the first embodiment shown in FIGS. 1-3, each guide element is in the form of a row of triangular projections 10. Each row 10 includes five triangular projections 11 aligned along a transverse axis Y perpendicular to the repeat axis X and to the vertical axis Z. In other embodiments, each row 10 may comprise two, three, four, or more than five triangular projections 11.

Each triangular projection 11 has a base 12 and a vertex 13. In each row 10, the bases 12 form a first guide surface 14, perpendicular to the base surface 7 and to the repeat axis X, and the vertex 13 form a second guide surface 16, perpendicular to the base surface 7 and presenting a succession of concavities to form a row of teeth.

The first guide surface 14 of one of the rows of triangular projections 10 is facing the second guide surface 16 of the adjacent row of triangular projections 10. Moreover, the triangular projections 11 of two adjacent rows 10 have aligned bases 12 and vertex 13. The rows of triangular projections 10 thus form a plurality of pairs of guide surfaces adjacent along the repeat axis X and define a repeating pattern along this repeat axis X.

Each of the pairs of guide surfaces comprises one of the first guide surfaces 14 and the second guide surface 16 which faces it, defining a guide space between them. In the first embodiment, the guide comprises a plurality of substantially triangular cavities 15 each with a base 17 formed on the first guide surface 14 of one of the rows of triangular projections 10 and a vertex 18 formed on the second guide surface 16 of the row of adjacent triangular projections 10. In particular, for each cavity 15, the base 17 is formed by portions of the bases 12 of two triangular projections 11 of one of the rows 10 and the vertex 18 is formed by two lateral walls converging towards each other of two triangular projections 11 of the adjacent row 10. The repeating pattern thus presents a series of cavities 15 along the repeat axis X.

Each cavity 15 is adapted to receive at least a portion of one of the cells 3. The cavity 15 has a maximum dimension, measured between the first 14 and second 16 guide surfaces, of less than 200 μm, preferably less than 100 μm. Advantageously, the maximum dimension of the cavity 15 substantially corresponds to a size of the cells 3 and is, for example, between 5 μm and 60 μm, preferably between 15 μm and 30 μm. Moreover, the cavity 15 has a depth, measured perpendicularly to the base surface 7, of less than 200 μm, preferably less than 100 μm. Advantageously, the depth of the cavity 15 is less than a size of the cells 3, for example less than 20 μm, or even less than 6 μm. For example, each cavity 15 has a depth of 2 μm and is in the shape of an equilateral triangle where side B measures 32 μm, which is a maximum distance between the first 14 and second 16 guide surfaces of 27.71 μm.

In the embodiment shown, the triangular projections 11 are represented as touching one another within the same row 10 and between two adjacent rows 10. Gaps between the triangular projections 11 may be provided, however, to adjust the size of the cavity 15. In addition, each row 10 has been represented with a plurality of cavities 15, although each row 10 could comprise only one cavity 15.

Such a three-dimensional structure may be achieved, for example, by photolithography, optionally followed by an etching step, or by any microfabrication method.

A method of guiding cell migration which makes use of the substrate 5 described above is now described in relation to FIGS. 2 and 3.

The textured surface 6 of the substrate 5 is placed facing the support surface 2 and in contact with the cells 3 arranged on the support surface 2 so that the cells 3 are confined between the support surface 2 and the textured surface 6. Confinement of the cells 3 further reinforces their guidance, in particular when the substrate 5 on which the cells 3 are conveyed is not adhesive.

The support surface 2 and the textured surface 6 are spaced apart by a distance of between 0 μm and 10 μm, preferably between 3 μm and 6 μm, so that the thickness of the cell 3 after confinement is at least between 3 μm and 6 μm to allow its migration. The base surface 7 of the substrate 5 is placed at a distance D from the support surface 2, for example 5 μm, and the triangular projections 11 are placed at a distance d from the support surface 2 which is smaller than the distance D between the base surface 7 and the support surface 2, for example 3 μm.

The support surface 2 which the cells 3 rest upon may be an artificial surface such as a cell culture surface (a gel for example), a glass slide, the interior of a microfluidic channel, or a surface of the natural environment of said cells such as the surface of living tissue or the surface of a wound.

When the cells are conveyed on a support bearing the support surface 2 and having a rigidity greater than about 20 kPa, it is desirable, in the context of the present invention, that at least one of the surfaces chosen from among the support surface 2 and the textured surface 6 comprises at least one additional projection, not shown, for controlling a distance between the support surface 2 and the textured surface 6 and thus avoiding damage to the cells 3. The height of these projections is measured from the surface on which they are arranged. The additional projection may be in the form of one or more pillars with a diameter of between 100 μm and 500 μm and with a height of less than 10 μm, preferably between 3 μm and 6 μm, and in any event of a height such that the thickness of the cell 3 after confinement is at least between 3 and 6 μm.

Conversely, when the cells are conveyed on a "soft" support bearing the support surface 2, meaning that it has a stiffness of less than about 20 kPa, in particular between 100 Pa and 20 kPa, preferably between 500 Pa and 10 kPa, it is not necessary for it to have additional projections since the support surface 2 is sufficiently "soft" to prevent the cells 3 from being crushed by the substrate: the cells 3 define their confinement space by deforming the support surface 2. These "soft" supports are low stiffness gels or a cell layer. The gels used can be gels of artificial origin such as polyacrylamide (PAM) or polyethylene glycol diacrylate (PEGDA), or naturally occurring gels such as collagen, matrigel, or hyaluronic acid (HA). The rigidity of these gels can be adjusted through their composition and the cross-linking conditions.

Each cavity 15, of which the second guide surface 16 extends away from the first guide surface 14 along the repeat axis X, is oriented along a direction of anisotropy A1 that is parallel to the repeat axis X and runs directionally from the first surface guide 14 toward the second surface 16.

In each cavity 15, the first guide surface 14 is adapted to block movement of the cells 3 in a direction opposite to the second guide surface 16 and the second guide surface 16 is adapted to allow movement of the cells 3 in a direction opposite to the first guide surface 14.

The cavities 15 can then guide the movement of the cells 3 carried by the support surface 2 in the direction of anisotropy A1, which is along the direction of the repeat axis X from the base 17 to the vertex 18 of the cavity 15.

Figure 4:
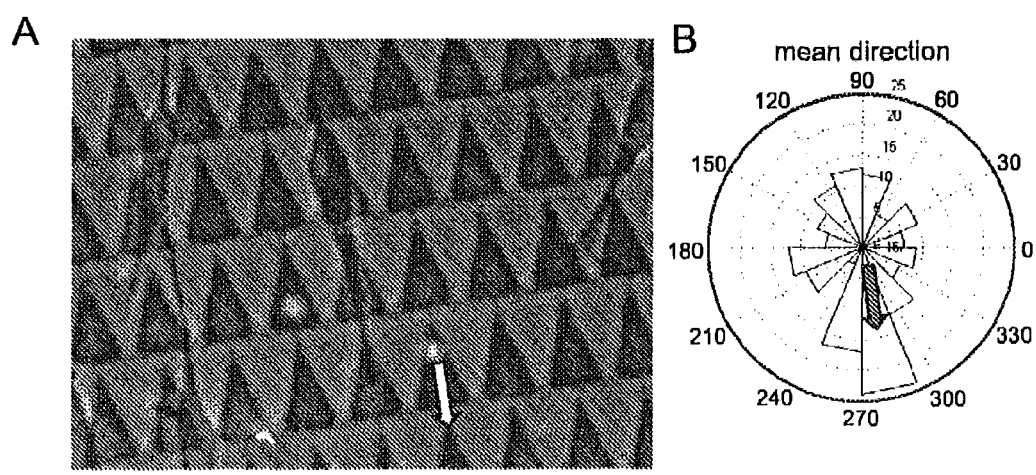
FIG. 4A is a phase contrast image of the cells confined under the triangular projections.
FIG. 4B is a histogram showing the induced bias in the direction of cell migration.

FIG. 4A is a phase contrast image of cells confined under the triangular projections 11. The light triangles in FIG. 4A represent the cavities 15, and the triangular projections 11 are indicated by the dark triangles. FIG. 4B is a histogram showing the bias induced in the direction of migration of 167 cells confined under the structure described above, after 24 hours of migration. In FIGS. 4A and 4B, an arrow indicates the direction of the points of the triangular cavities 15.

The histogram shows the preferred direction of migration corresponding to the direction in which the cavities 15 are oriented.

The guiding method which has just been described utilizes a textured surface 6 in which the three-dimensional structure 8 or texture is biased in a direction referred to as the direction of anisotropy A1, so that the cells 3 can apply pressure more easily in one direction (here, towards the second guide surface 16) than in another (here, towards the first guide surface 14), or can more easily cling in one direction (here, towards the first guide surface 14) than in another (here, towards the second guide surface 16), or can be more easily deformed in one direction (here, towards the second guide surface 16) than in another (here, towards the first guide surface 14). Such anisotropy in the interaction between the cell 3 and the substrate 5 induces a preferred direction of migration, modeled on the structure referred to as a Brownian ratchet, described above.

In the embodiment described above, the direction of anisotropy A1 is defined by a concavity facing the first guide surface 14 and formed by two straight side walls converging towards each other. Other shapes may, however, be provided for the guide space to form a concavity facing the first guide surface 14 and thus define a direction of anisotropy A1 parallel to the repeat axis X, running from the first guide surface 14 to the second guide surface 16. For example, the concavity may be rounded, in particular formed by two curving side walls converging toward each other or by a single curving side wall.

The invention is not limited to creating a concavity to orient the direction of anisotropy A1 parallel to the repeat axis X, from the first guide surface 14 toward the second guide surface 16.

Figure 5:
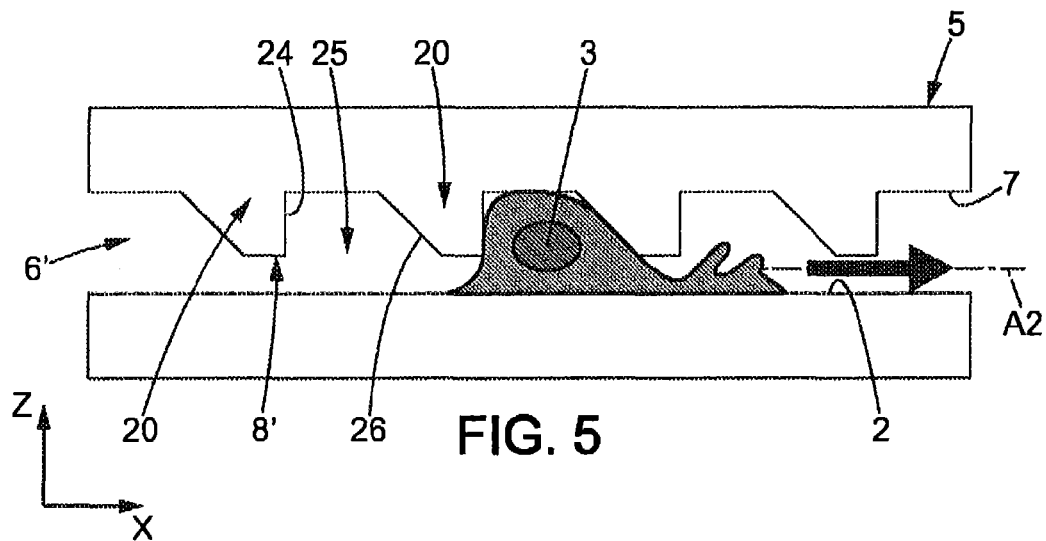
FIG. 5 is a cross-sectional representation of the guiding device comprising a substrate according to a variant of the first embodiment of FIG. 1, the substrate having a textured surface with a plurality of elongated projections defining a series of guide grooves adjacent along the repeat axis, the guide grooves guiding the movement of cells carried by the support surface in one of the directions of the repeat axis.

For example, in a variant represented in FIG. 5, the guide elements are implemented as elongated projections 20 each extending along the transverse axis Y, perpendicular to the repeat axis X. Each elongated projection 20 bears a first guide surface 24, perpendicular to the repeat axis X, and a second guide surface 26 that slopes relative to a plane perpendicular to the base surface 7.

In this variant, only the textured surface 6' of the substrate 5 differs from the textured surface described above. The detailed description of the substrate 5 and other similar elements will therefore not be repeated, and one can refer to the description already provided for further details.

As described above, the first guide surface 24 of one of the elongated projections 20 is placed facing the second guide surface 26 of the adjacent elongated projection 20. The elongated projections 20 thus form a plurality of pairs of adjacent guide surfaces along the repeat axis X and define a repeating pattern along this repeat axis X.

Each of the pairs of guide surfaces includes one of the first guide surfaces 24 and the second guide surface 26 which faces it, defining a guide space between them.

In this variant of the first embodiment, the guide space comprises a groove 25 extending along the transverse axis Y. The repeating pattern then has a succession of grooves 25 along the repeat axis X. Each groove 25 is adapted to receive at least a portion of one of the cells 3. The groove 25 has a maximum dimension, measured at the bottom of the groove 25 between the first 24 and second 26 guide surfaces, that is less than 200 µm, preferably less than 100 µm. Advantageously, the maximum dimension of the groove 25 substantially corresponds to a size of the cells 3 and is, for example, between 5 µm and 60 µm, preferably between 15 µm and 30 µm. The groove 25 has a depth, measured perpendicularly to the base surface 7, of less than 200 µm, preferably less than 100 µm. Advantageously, the depth of the groove 25 is less than a size of the cells 3, for example less than 20 µm, or even less than 6 µm.

Such a three-dimensional structure may be achieved, for example, by photolithography, followed optionally by a step of anisotropic etching such as RIE, ICP or DRIE, while tilting the sample during the photolithography or etching to obtain the sloped faces, or by gray-tone lithography.

As represented in FIG. 5, each groove 25 has its second guide surface 26 diverging from its first guide surface 24 along the repeat axis X, and is oriented in a direction of anisotropy A2 parallel to the repeat axis X that is directionally from the first guide surface 24 toward the second guide surface 26. In each groove 25, the first guide surface 24 blocks movement of the cells 3 in the direction opposite to the second guide surface 26 and the second guide surface 26 allows movement of the cells 3 in the direction opposite to the first guide surface 24. The grooves 25 thus guide movement of the cells 3 carried by the support surface 2 in the direction of anisotropy A2, meaning in the direction of the repeat axis X and from the first guide surface 24 towards the second guide surface 26.

Figure 6:
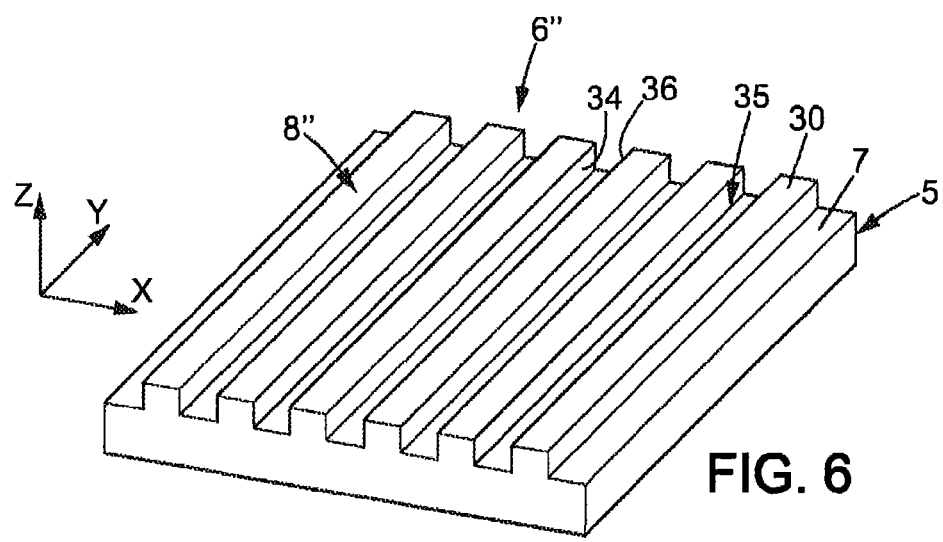
FIG. 6 is a perspective representation of a second embodiment of a substrate of a cell migration guiding device, the substrate having a textured surface with a plurality of elongated projections defining a series of guide grooves adjacent along the repeat axis, the guide grooves guiding the movement of cells carried by the support surface in one of the directions of an axis perpendicular to the repeat axis.
Figure 7:
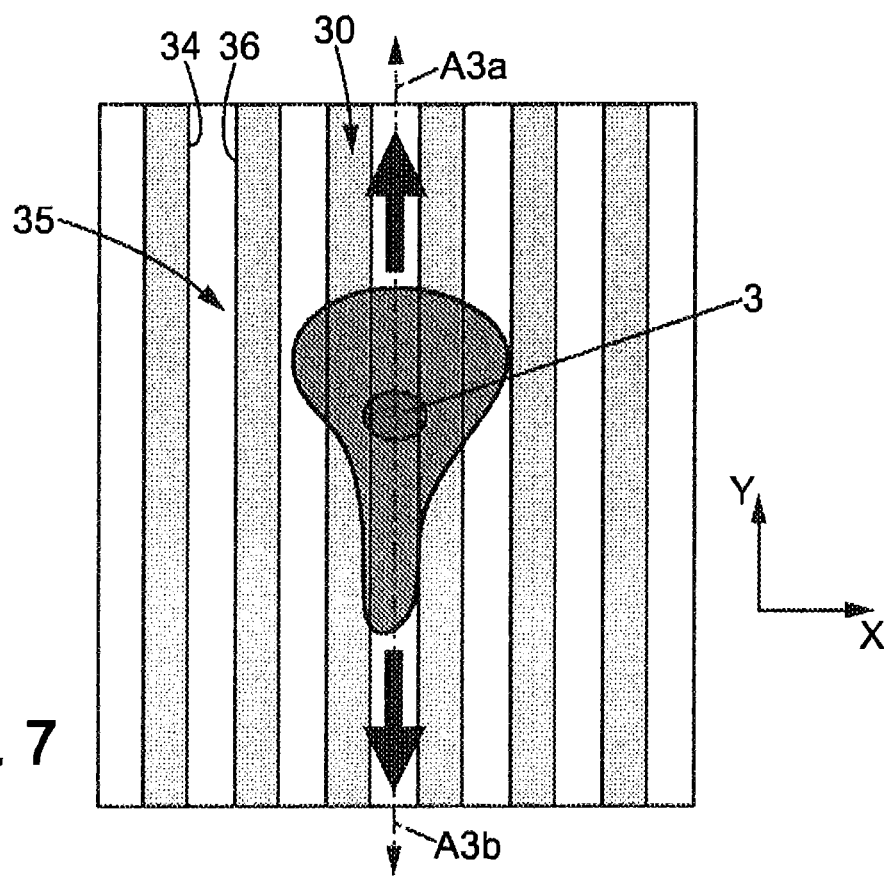
FIG. 7 is a top view representation of the substrate of FIG. 1, in which the textured surface is facing a support surface in a guiding device, with FIG. 7 illustrating the movement of a cell between a support surface and the textured surface of the substrate.

FIGS. 6 and 7 show a second embodiment of the invention where the guide spaces 35 are oriented in a direction of anisotropy A3a, A3b, which extends along the transverse axis Y, perpendicular to the repeat axis X, in a manner that guides the movement of the cells 3 along the transverse axis Y.

In this second embodiment, only the textured surface 6" of the substrate 5 is different from that of the first embodiment described above. The detailed description of the substrate 5 and other similar elements will therefore not be repeated, and one can refer to the description already provided in relation to the first embodiment for further details.

The guide elements are implemented as elongated projections 30, each extending along the transverse axis Y. Each elongated projection 30 has first 34 and second 36 guide surfaces, perpendicular to the repeat axis X.

As described above, the first guide surface 34 of one of the elongated projections 30 is placed facing the second guide surface 36 of the adjacent elongated projection 30. The elongated projections 30 thus form between them a plurality of pairs of guide surfaces adjacent to each other along the repeat axis X and define a repeating pattern along this repeat axis X.

Each of the pairs of guide surfaces includes one of the first guide surfaces 34 and the second guide surface 36 which faces it, defining a guide space between them.

In this second embodiment, the guide space comprises a groove 35 which extends along the transverse axis Y. The repeating pattern then has a succession of grooves 35 along the repeat axis X. Each of the grooves 35 is adapted to receive at least a portion of one of the cells 3. The groove 35 has a maximum dimension, measured between the first 34 and second 36 guide surfaces, that is less than 200 µm, preferably less than 100 µm. Advantageously, the maximum dimension of the groove 35 substantially corresponds to a size of the cells 3 and is, for example, between 5 μm and 60 μm, preferably between 15 μm and 30 μm. The groove 35 has a depth, measured perpendicularly to the base surface 7, of less than 200 μm, preferably less than 100 μm. Advantageously, the depth of the groove 35 is less than a size of the cells 3, for example less than 20 μm, or even less than 6 μm.

Each groove 35 for which the first 34 and second 36 guide surfaces extend along the transverse axis Y may be oriented along one of the directions of anisotropy A3a, A3b parallel to the transverse axis Y, by any suitable means, for example notches or ratchets arranged on the first 34 and second 36 guide surfaces or on the bottom of the groove 35. In each groove 35, the first 34 and second 36 guide surfaces block movement of the cells 3 in either direction of the repeat axis X. The grooves 35 thus guide movement of the cells 3 carried by the support surface 2 in one of the directions of anisotropy A3a, A3b.

The guiding device 1 according to the invention has numerous applications in guiding the migration of cells in vivo or in vitro.

Guiding cell migration in vitro is understood to mean guiding the migration of cells in culture in a completely artificial medium. The cells may, for example, be grown on an artificial support surface such as a cell culture dish, the textured surface then being applied to the support surface in order to confine the cells. In another embodiment, the textured surface can be incorporated into one of the faces of a microfluidic channel in order to guide cell migration in said microfluidic channel. The textured surfaces of the device according to the invention can be used either for the study of biological and physical processes of cell migration and proliferation in culture, or for sorting cells by separating the cells according to their migration characteristics. Alternatively, the device of the invention can be used to guide cells on two-dimensional or three-dimensional substrates at least partially covered with a textured guide surface in order to produce artificial organs (tissue engineering). The device according to the invention can find applications in any field which requires guiding cells artificially and regardless of their chemotactic behavior.

Guiding cell migration in vivo is understood to mean guiding the proliferation and migration of cells in a living being, for example humans. In this case, the support surface consists of the natural physiological medium of the cells, to which the textured surface is applied. In a preferred embodiment of guiding cell migration in vivo, the textured surface can be used to guide the cells present at the surface of a wound in order to encourage cell distribution over the wound. The device is then a dressing having microstructures on its surface. In another embodiment of guiding cell migration in vivo, the textured surface can be used to guide the cells around an prosthesis in order to facilitate the distribution of cells around the prosthesis. According to yet another embodiment of guiding cell migration in vivo, the textured surface can be used to guide the cells around an internal dressing or film placed inside the body of a living being in order to encourage the distribution of cells in or around an organ.

In one particular application, the guiding device may advantageously be used in vivo, as a dressing to promote wound healing. Aside from the particularly advantageous application as a wound dressing, the guiding device according to the invention has applications as an implant, prosthesis, support for artificial tissue, microfluidic channel, or lab-on-a-chip with integrated channels.

The invention claimed is:

1. A device for guiding cell migration, comprising a support surface provided with cells, and a substrate, said substrate having a textured surface placed facing the support surface at a distance along a vertical direction, said textured surface being in contact with the cells placed on the support surface such that the cells are confined in the vertical direction between the support surface and the textured surface, said textured surface having a base surface and an anisotropic three-dimensional structure presenting a repeating pattern along a repeat axis perpendicular to the vertical direction, said repeating pattern having a succession of guide spaces adjacent to one another along the repeat axis, the anisotropic three-dimensional structure comprising a plurality of pairs of guide surfaces, said pairs of guide surfaces being adjacent to each other along the repeat axis and defining the repeating pattern, each pair comprising first and second guide surfaces which extend from the base surface facing one another and which define between them one of the guide spaces, each of said guide spaces being capable of receiving at least a portion of one of the cells and being oriented in a direction of anisotropy perpendicular to the vertical direction in order to guide movement of the cells in the direction of anisotropy.

2. The guiding device according to claim 1, wherein the anisotropic three-dimensional structure comprises a plurality of guide elements projecting from the base surface, said guide elements being adjacent to each other along the repeat axis and each carrying one of the first guide surfaces and one of the second guide surfaces, the first guide surface of one of the guide elements facing the second guide surface of the adjacent guide element.

3. The guiding device according to claim 1, wherein the first and second guide surfaces of each pair are adapted so that the direction of anisotropy extends along the repeat axis.

4. The guiding device according to claim 3, wherein in each pair of guide surfaces, the first guide surface is adapted to block movement of the cells in a direction opposite to the second guide surface and the second guide surface is adapted to allow movement of the cells in a direction opposite to the first guide surface, such that the orientation of the direction of anisotropy is from the first guide surface towards the second guide surface.

5. The guiding device according to claim 4, wherein the first guide surface is perpendicular to the repeat axis and the second guide surface extends away from the first guide surface along the repeat axis.

6. The guiding device according to claim 5, wherein the second guide surface is perpendicular to the base surface and has a concavity directed towards the first guide surface.

7. The guiding device according to claim 6, wherein the anisotropic three-dimensional structure comprises a plurality of rows of triangular projections adjacent along the repeat axis, each of said rows comprising at least two projections aligned along a transverse axis perpendicular to the repeat axis, each of the guide spaces comprising a substantially triangular cavity with a base formed on the first guide surface of one of the rows of triangular projections and a vertex formed on the second guide surface of the adjacent row of triangular projections.

8. The guiding device according to claim 5, wherein the first guide surface is perpendicular to the repeat axis and the second guide surface is sloped relative to a plane perpendicular to the base surface.

9. The guiding device according to claim 1, wherein the first and second guide surfaces of each pair are adapted so that the direction of anisotropy extends along a transverse axis perpendicular to the repeat axis.

10. The guiding device according to claim 9, wherein, in each pair of guide surfaces, the first and second guide surfaces are adapted to block the movement of the cells in either direction of the repeat axis.

11. The guiding device according to claim 10, wherein the anisotropic three-dimensional structure comprises a plurality of elongated projections adjacent along the repeat axis, each of said elongated projections extending along the transverse axis, each guide space comprising a groove between the first guide surface of one of the elongated projections and the second guide surface of the adjacent elongated projection.

12. The guiding device according to claim 1, wherein the guide space has a maximum dimension, measured between the first and second guide surfaces, that is less than 200 μm.

13. The guiding device according to claim 1, wherein the guide space has a depth measured along the vertical direction of less than 200 μm.

14. The guiding device according to claim 1, wherein the substrate is non-adhesive to the cell.

15. The guiding device according to claim 14, wherein the non-adhesive substrate consists of a non-adhesive material.

16. The guiding device according to claim 1, wherein the substrate is adhesive to the cell.

17. The guiding device according to claim 1, wherein the support surface on which the cells move is an artificial surface chosen among a cell culture surface, a glass slide, and the interior of a microfluidic channel.

18. The guiding device according to claim 1, wherein the support surface and the textured surface are spaced apart by a distance of less than 10 μm.

19. The guiding device according to claim 18, wherein at least one of the surfaces chosen from among the support surface and the textured surface comprises at least one additional projection for controlling the distance between the support surface and the textured surface.

20. The guiding device according to claim 19, wherein the additional projection is in the form of a pillar with a diameter of between 100 μm and 500 μm and a height of less than 10 μm.

21. The guiding device according to claim 1, provided in the form of a dressing, an implant, a prosthesis, a support for artificial tissue, a microfluidic channel, or a lab-on-a-chip with integrated channels.

22. A method of guiding cell migration using the guiding device according to claim 1, said method comprising a step of bringing the cells placed on the support surface in contact with the textured surface of the substrate so that the cells are confined between the support surface and the textured surface, the cells moving in the direction of anisotropy.

23. The guiding device according to claim 12, wherein the maximum dimension of the guide space is less than 100 μm.

24. The guiding device according to claim 12, wherein the maximum dimension of the guide space is between 5 μm and 60 μm.

25. The guiding device according to claim 12, wherein the maximum dimension of the guide space is between 15 μm and 30 μm.

26. The guiding device according to claim 13, wherein the depth of the guide space is less than 100 μm.

27. The guiding device according to claim 13, wherein the depth of the guide space is less than 6 μm.

28. The guiding device according to claim 15, wherein the non-adhesive material is a fluoropolymer.

29. The guiding device according to claim 14, wherein the non-adhesive substrate consists of a material rendered non-adhesive by chemical treatment.

30. The guiding device according to claim 29, wherein the non-adhesive substrate consists of a material rendered non-adhesive by grafting of polyethylene glycol (PEG) molecules.

31. The guiding device according to claim 1, wherein the support surface on which the cells move is a surface of the natural environment of said cells chosen among the surface of living tissue or the surface of a wound.

32. The guiding device according to claim 18, wherein the support surface and the textured surface are spaced apart by a distance between 3 μm and 6 μm.

33. The guiding device according to claim 20, wherein the height of the pillar is between 3 μm and 6 μm.

* * * * *